(12) United States Patent
Bush et al.

(10) Patent No.: US 6,859,738 B2
(45) Date of Patent: Feb. 22, 2005

(54) METHOD AND SYSTEM FOR PREDICTING INITIAL ANALYTE VALUES IN STORED SAMPLES

(75) Inventors: Valerie Bush, Wanaque, NJ (US); Karen Byron, Ringwood, NJ (US); James King, Monsey, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/996,801

(22) Filed: Nov. 30, 2001

(65) Prior Publication Data

US 2003/0033092 A1 Feb. 13, 2003

Related U.S. Application Data

(63) Continuation-in-part of application No. PCT/US01/43352, filed on Nov. 21, 2001.
(60) Provisional application No. 60/308,987, filed on Jul. 31, 2001.

(51) Int. Cl.[7] .............................................. G01N 31/00
(52) U.S. Cl. .......................................... 702/25; 600/347
(58) Field of Search .................... 702/25, 66; 600/347, 600/345; 435/6

(56) References Cited

U.S. PATENT DOCUMENTS

| | | | |
|---|---|---|---|
| 6,303,305 B1 * | 10/2001 | Wittwer et al. ................ | 435/6 |
| 2001/0016682 A1 * | 8/2001 | Berner et al. ................ | 600/345 |
| 2002/0026110 A1 * | 2/2002 | Parris et al. ................ | 600/347 |
| 2003/0078746 A1 * | 4/2003 | Samsoondar ................ | 702/66 |

OTHER PUBLICATIONS

Mary M. Christopher, Sharon O'Neill, "Effect of Specimen Collection and Storage on Blood Glucose and Lactate Concentrations in Healthy, Hyperthyroid and Diabetic Cats", Veterenary Clinical Pathology, vol. 29, No. 1, 2000, pp. 22–28.

Christina Westby, Ingrid Alfheim, Catrine Kvam, Marte Hveem, "The Stability of Homocysteine Concentration in Blood Samples", Poster Presented at IFCC, Jul. 1999 Florence, p. 2.

Jamees G. Donnelly, Steven J. Soldin, Daniel A. Nealon, Jocelyn M. Hicks: "Stability of Twenty–Five Analytes in Human Serum at 22° C., 4° C. and – 20° C.", Pediatric Pathology & Laboratory Medicine: Journal of the Society for Pediatric Pathology, vol. 15, No. 6, Nov. 1995—Dec. 1995, pp. 869–874.

Egger G. et al., "Changes in the Polymorphonuclear Leukocyte Function of Blood Samples Induced by Storage Time, Temperature and Agitation", Journal of Immunological Methods, Elsevier Science Publishers B.V., Amsterdam, NL. vol. 206, No. 1–2, Aug. 7, 1997, pp. 61–71.

Susan J. Tornquist, Linda Dodson, Dirkv. Lanning, "Effect of Temperature, Storage Time, and Sample Type on Sorbitol Dehydrogenase Activity in Llama Serum and Plasma" Veterinary Clinical Pathology, vol. 1, No. 29, 2000, pp. 16–18.

* cited by examiner

*Primary Examiner*—John Barlow
*Assistant Examiner*—Xiuqin Sun
(74) *Attorney, Agent, or Firm*—Alan W. Fiedler (57) ABSTRACT

A system and method are provided for estimating the initial level of an analyte in a sample based on an actual level observed, a time of storage of the sample, a storage temperature, and a type of container in which said sample is stored. Equations are generated for a particular analyte based on observations of actual analyte levels initially after a sample is drawn, as well as at various times thereafter. The time of storage, the temperature of storage, and the type of container are observed along with actual analyte level in each observation. The equations generated are considered useful if the estimated initial values are more accurate than the actual observed final values.

18 Claims, 9 Drawing Sheets

METHOD AND SYSTEM FOR PREDICTING INITIAL ANALYTE VALUES IN STORED SAMPLES

This application claims priority from U.S. Provisional Application Ser. No. 60/308,987, filed Jul. 31, 2001, the contents of which are expressly incorporated herein by reference in there entirety. This application is also a continuation-in-part of International Application No. PCT/US01/43352, filed Nov. 21, 2001.

FIELD OF THE INVENTION

The present invention is related to biological and chemical sample analysis. In particular, but not by way of limitation, the present invention is related to a system and method for predicting initial values of common analytes in a blood sample, after the sample has been stored for a known period of time at a known temperature and in a known type of sample container.

BACKGROUND OF THE INVENTION

Many central laboratories receive specimens from remote collection stations, satellite laboratories, physician office laboratories (POLs), home health care nurses, and the like. Laboratory environments have changed such that more and more specimens are collected remotely and transported to core labs for analysis. In these situations, the specimens may not reach the testing laboratory until several hours or days after collection. Furthermore, the conditions of transport may vary widely. Additionally, stored specimens are often retrieved for add-on or repeat testing. In each of these situations, time and temperature can influence analyte stability, and hence the actual observed value of a specimen tested after transportation and/or storage.

Previous studies have been conducted to evaluate the stability of analytes. However, in those studies, either time or temperature was fixed. In the real world, the laboratory may have little control over the transport and storage conditions of specimens from remote locations.

Analyte values are used by physicians and medical professionals to make diagnoses of diseases and other health related problems. Furthermore, analyte values are used in medical treatments, for therapeutic monitoring, to measure response to a treatment or therapy, and to follow the progression of a disease. The effectiveness of these uses are dependent on accurate determinations of analyte values. Because analyte values can change over time, any determination made based on observed analyte values at a later time can be affected by the degree of analyte degradation since the sample was taken. Therefore, it would be desirable to have an accurate model for estimating the initial values of analytes in a blood sample, given knowledge of the transport and storage conditions. Such conditions include the type of container used to store the sample, the temperature at which the sample was stored, and the time elapsed from when the sample was obtained to when it is actually tested.

Furthermore, it would be desirable to have testing equipment which incorporated such a model, to provide not only the actual observed value for a particular analyte, but also an accurate estimate of what the value was when the sample was taken, given knowledge of the transport and storage conditions, as discussed above.

SUMMARY OF THE INVENTION

The above mentioned disadvantages are overcome and other advantages are realized by the present invention, which relates to a method for predicting an initial value of an analyte in a sample, particularly but not exclusively a blood sample. The method involves the steps of making a plurality of observations on a plurality of known samples, wherein each observation includes a plurality of variables associated with the sample. The variables include the actual analyte level at the time the sample was taken, the time since the sample was taken, the temperature at which the sample was stored, the type of tube or container in which the sample was stored, and the measured analyte level obtained after the storage time. The method also includes generating a model or equation which closely approximates the plurality of observations. The method also involves measuring the actual analyte level in an unknown sample, inputting the container type, storage time and storage temperature into the equation, and finally solving the equation to obtain the estimated initial analyte value.

The invention further comprises a method of predicting an initial analyte value given a sample that has been stored for a known time at a known temperature and in a known type of container. The method comprises the steps of determining the actual level of an analyte in a sample. Inputting data associated with the sample, including the storage time, storage temperature and container type, and applying the data to a predictive model or equation. The method further involves solving the equations to obtain an estimated initial analyte value.

The invention also comprises a system for estimating an initial value of an analyte in a sample. The system comprises a common chemistry analyzer which is adapted to analyze the actual level of one or more analytes in the sample. The system further comprises an estimator which is adapted to estimate the initial level analyte in the sample based on values including the actual level of the analyte measured by the analyzer, the storage time, the storage temperature, and the tube or container type.

The invention further comprises a method of generating a predictive model for predicting the initial value of an analyte in a sample. The samples are understood to preferably be blood samples, but the invention is not limited to blood samples. The method comprises the steps of collecting a plurality of samples, testing each sample for an initial value of an analyte, storing at least one sample at each of a plurality of storage temperatures, testing each sample for subsequent levels of the analyte after known time intervals, analyzing the data collected based on a polynomial regression model, and generating a predictive model or equation based on the results.

The invention further relates to a computer-readable medium of instructions which is adapted to control a system to generate a predicted initial analyte value. A first set of instructions is adapted to control the system to collect a plurality of data associated with a sample, the data comprising an actual analyte value, a time of storage, a temperature of storage, and a type of container in which the sample was stored. A second set of instructions is adapted to control the system to apply the data to a predictive model and to calculate an estimated initial analyte value. A third set of instructions is adapted to control the system to output the estimated initial analyte value.

The computer-readable medium of instructions can be further adapted to generate the predictive model. In this case, the computer-readable medium of instructions further includes a fourth set of instructions adapted to control the system to collect a plurality of data associated with a known set of samples. Each sample is associated with data including an actual initial analyte value, an actual subsequent analyte value, a time of storage, a temperature of storage, and a type of container. A fifth set of instructions is adapted to control the system to generate the predictive model from the data associated with the known set of samples.

BRIEF DESCRIPTION OF THE DRAWINGS

The invention will be further understood with reference to the attached drawing figures, in which.

Throughout the drawing figures, it will be understood that like numerals refer to like structures or steps.

DETAILED DESCRIPTION OF THE PREFERRED EMBODIMENT

The following description of the presently contemplated best mode of practicing the invention is not to be taken in a limiting sense, but is provided merely for the purpose of describing the general principles of the invention. The scope of the invention should be determined by reference to the claims.

Figure 1:
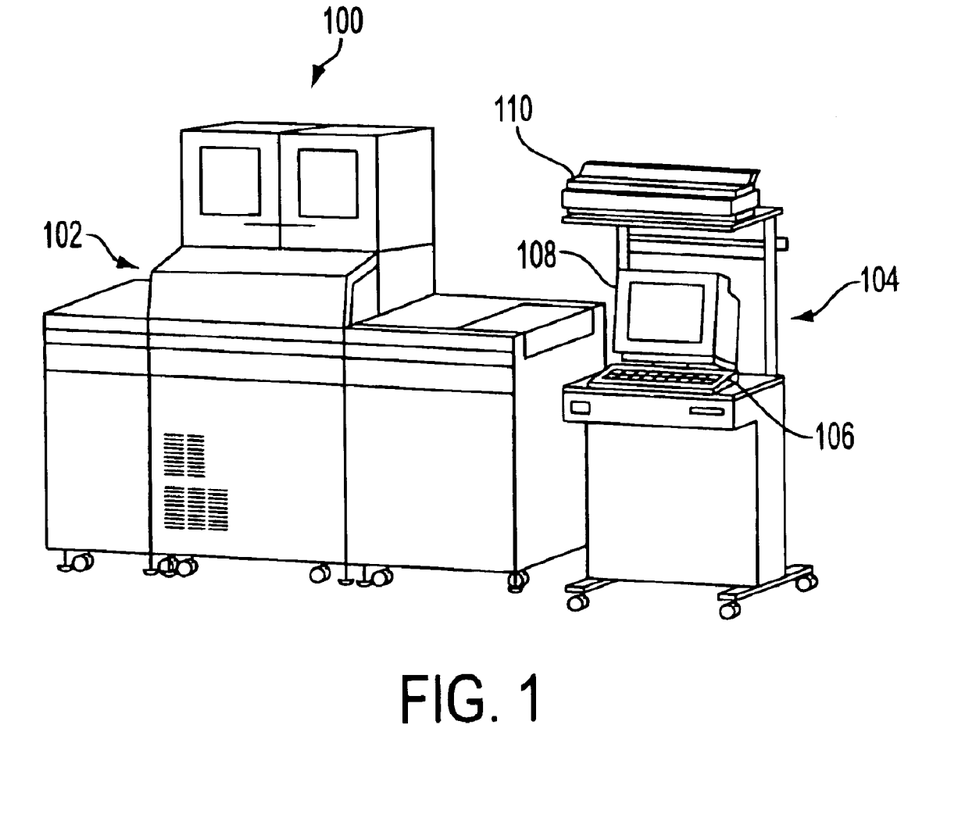
FIG. 1 illustrates a system according to an embodiment of the present invention.

FIG. 1 shows a system according to an embodiment of the present invention. The system 100 includes blood analyzing equipment 102, as well as a computer 104. The computer has input devices, such as the keyboard 106 shown, and output devices, such as the monitor 108 and printer 110 shown. It will be understood that a wide variety of input devices could be employed, as is known to those of skill in the art. For instance, the input devices could include bar code readers, RF tag readers, optical character recognition (OCR) equipment, and any other type of input device which could provide data to the computer 104. Similarly, the output devices shown include a monitor 108 and printer 110, and it should be understood that these are merely shown as examples, but that a wide variety of output devices are contemplated to be within the scope of the invention. Some input devices, such as a bar code reader, are particularly advantageous for their ability to input data associated with particular blood samples. Blood samples could be provided with bar codes containing data related to the sample, such as the actual time and date the sample was drawn, and the type of container used to hold the sample, and the temperature at which the sample was stored.

Of course it should be understood that while a system according to an embodiment of the invention is described above as including a computer, the invention is not intended to be limited to a computer system. Simplified implementations of the invention could include a spreadsheet with a set of formulas designed to calculate estimated initial analyte values from a set of input values, such as temperature and time of storage. Similarly, the invention could comprise a web page having input fields, and an application running on the web page's server which calculates estimated initial values of analytes from information input by a user remotely connected to the web page. The above examples are provided merely as illustrations, and are meant in no way to limit the scope of the invention.

As will be described in further detail below, the invention may be understood to comprise two phases. The first phase involves generating and validating predictive models for particular blood analytes, which accurately and reliably predict the initial value of an analyte in a blood sample, given the actual value measured at a later time, along with data including the storage time, storage temperature, and container type. The second phase involves employing the model on a new or unknown blood sample which has been stored for a known time at a known temperature in a known container, in order to obtain an accurate and reliable estimate of what a blood analyte's value was when the sample was first obtained.

Generating Predictive Model

Figure 2:
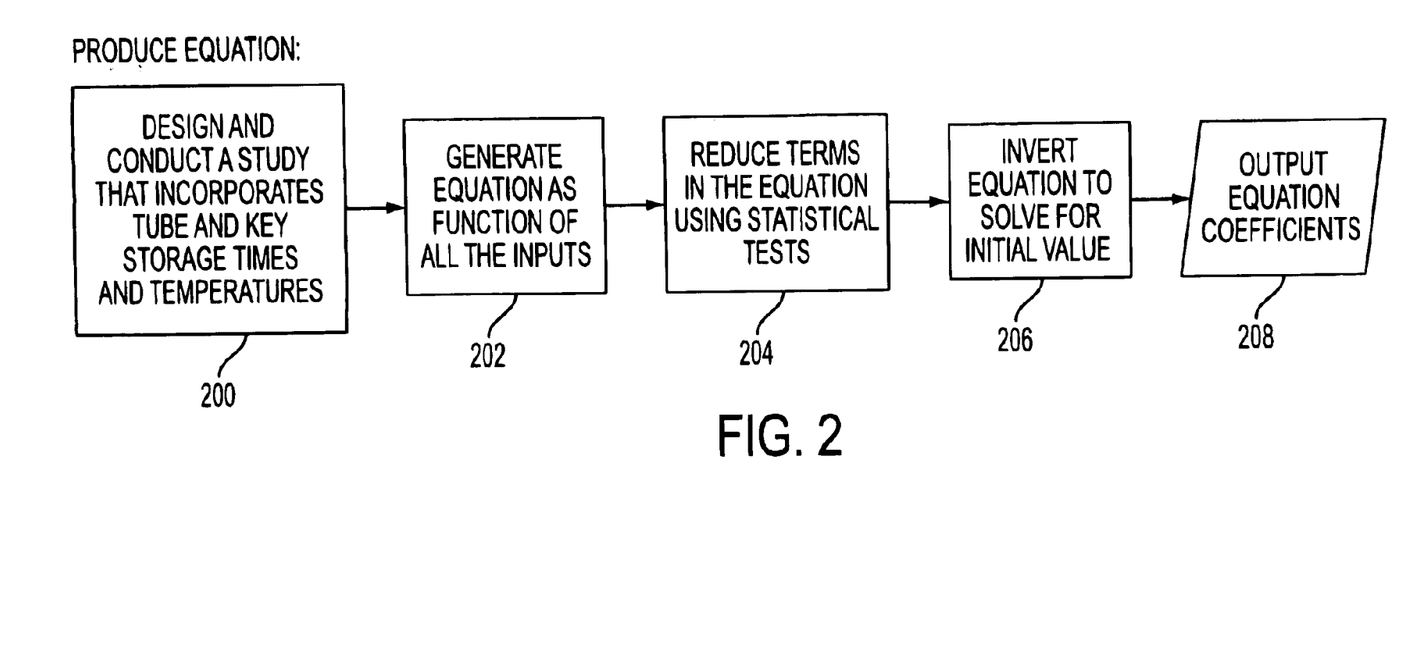
FIG. 2 is a flowchart depicting a method of producing a predictive model in accordance with an embodiment of the invention.

FIG. 2 is a flowchart illustrating the process of producing a predictive model, or equation, for a given analyte. The first step 200 in producing an equation for a particular blood analyte is to design and conduct a study that incorporates the significant variables, such as tube type, storage time, and storage temperature. Examples of a study will be described in greater detail below. Next, after the data is collected, the next step 202 is to generate an equation as a function of all of the inputs. This is done through statistical analysis of the data. A "best fit" equation is produced based on the observations made during the study. Next, statistical tests are used to reduce the terms in the equation at step 204. Next, the equation is inverted at step 206 to solve for the initial analyte value. Finally, at step 208, the coefficients of the equation representing the predictive model are outputted. More detailed information on regression analysis can be found in Dunn et al., *Basic Statistics: A Primer for the Biomedical Sciences, Third Edition* (New York: John Wiley & Sons, 2001), which is incorporated herein in its entirety.

The following is a description of an exemplary study conducted to generate predictive models, in accordance with the present invention. Twenty one common chemistry blood analytes were studied, along with two hormones. The analytes are listed in Table 1 below:

TABLE 1

| Analytes Tested/Validated | |
|---|---|
| Sodium | Total Protein |
| Potassium | Albumin |
| Chloride | Total Bilirubin |
| Bicarbonate | Alk. Phos. |
| Calcium | AST |
| Phosphate | ALT |
| Magnesium | GGT |
| Urea | Iron |
| Creatinine | Cholesterol |
| Uric Acid | Triglyceride |
| Glucose | Free T4 |
| Estradiol | |

It should be understood that the above list of analytes is exemplary in nature, and the invention could be applied to any variety of analytes.

In an exemplary embodiment of the present invention, blood is collected from a number of healthy donors, and placed into various different types of containers in randomized order. The tubes are stored at a variety of storage temperatures, such as −20° C., 4° C., 25° C. and 40° C. Actual analyte values are measured at various times such as 0, 8, 24, 48, and 168 hours after collection. From the healthy donors, a number of specimens are collected into the three different types of tubes, with a certain number of samples per tube type. Analysis of the common chemistry analytes is performed on a chemistry analyzer such as an Olympus 5000 analyzer. Hormones also can be analyzed on, for example, an Abbott Imx system.

Once the data is collected, a polynomial regression model is fit to the data. The model includes the significant factors allowed by the study. These can include quadratic terms, such as $Temp^2$ and $Time^2$, as well as interaction terms, such as $Temp*Time$.

FIGS. 3(a)–(d) illustrate four plots of raw data for analyte values over time. Each of the four Figures shows analyte values verses time for a particular storage temperature. Each of the four plots further illustrates a regression line which best fits the data. Statistical regression analysis is performed on the data collected for a particular analyte to generate a best fit line.

Figure 3A:
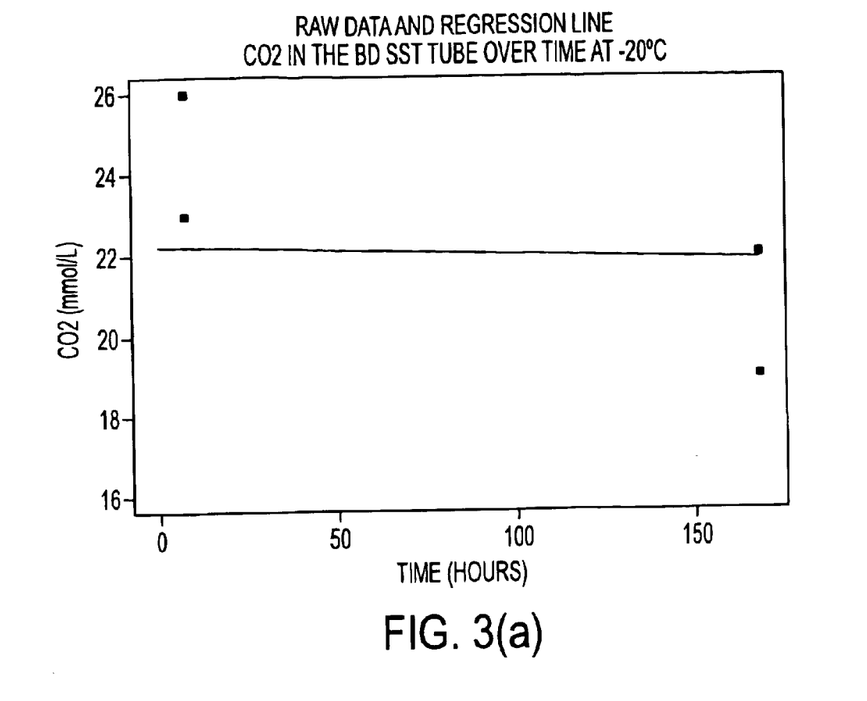
FIGS. 3(a)–(d) illustrate an exemplary regression line that fits raw data for a particular analyte at various temperatures over time.
Figure 3B:
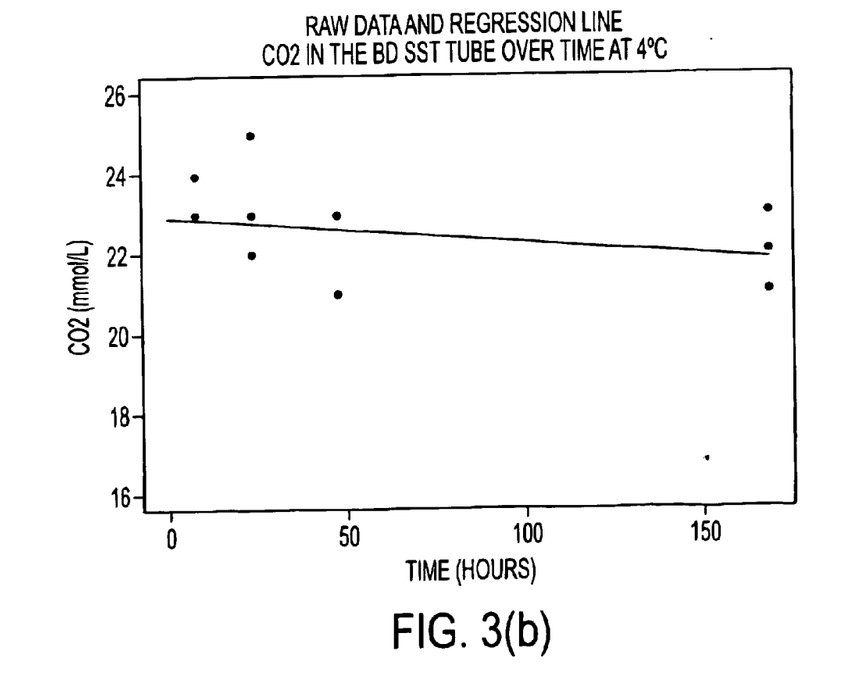
Figure 3C:
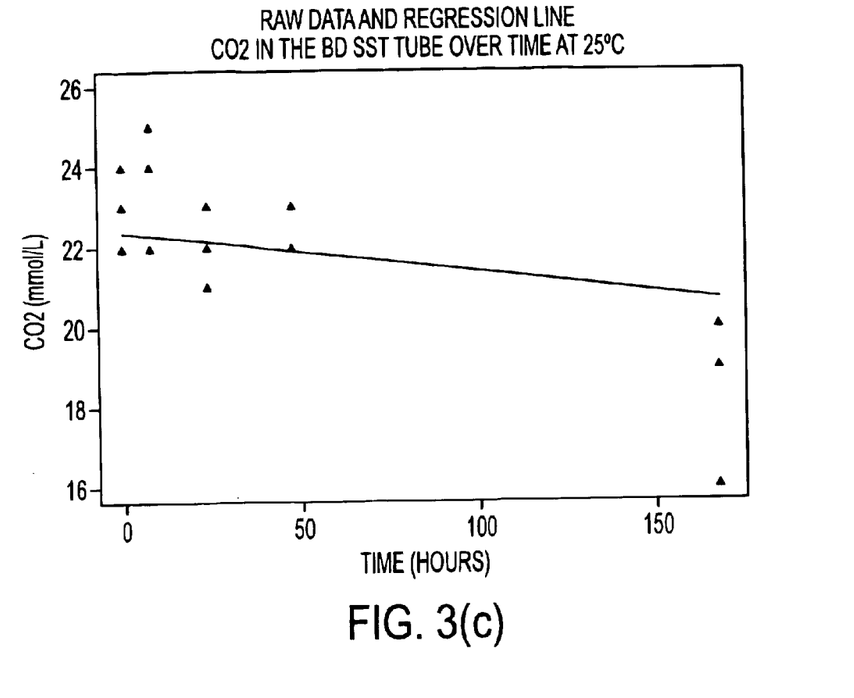
Figure 3D:
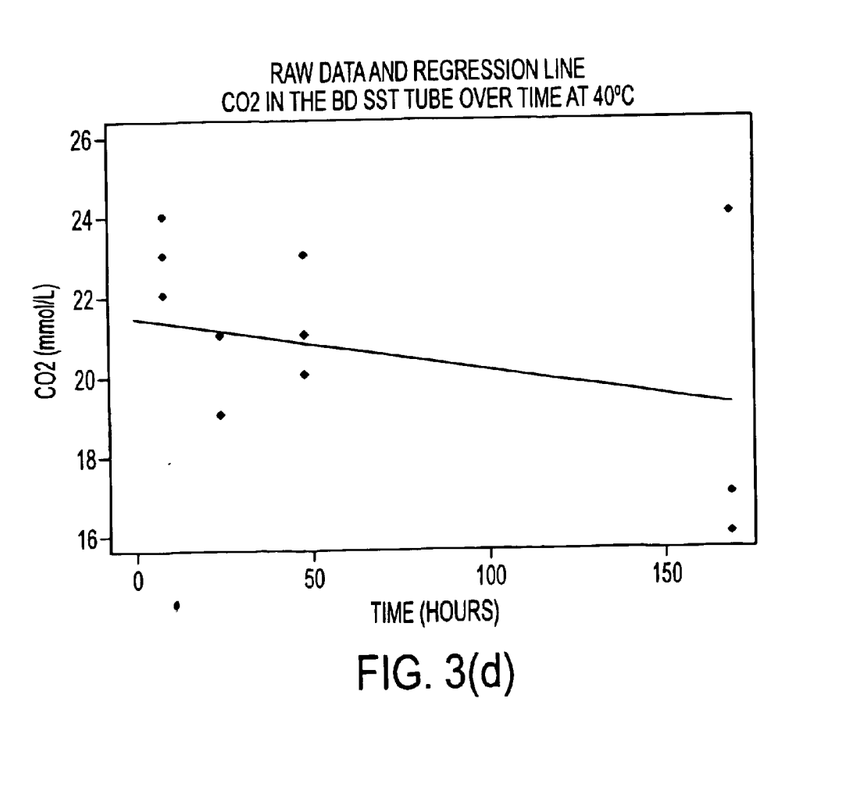
Figure 3E:
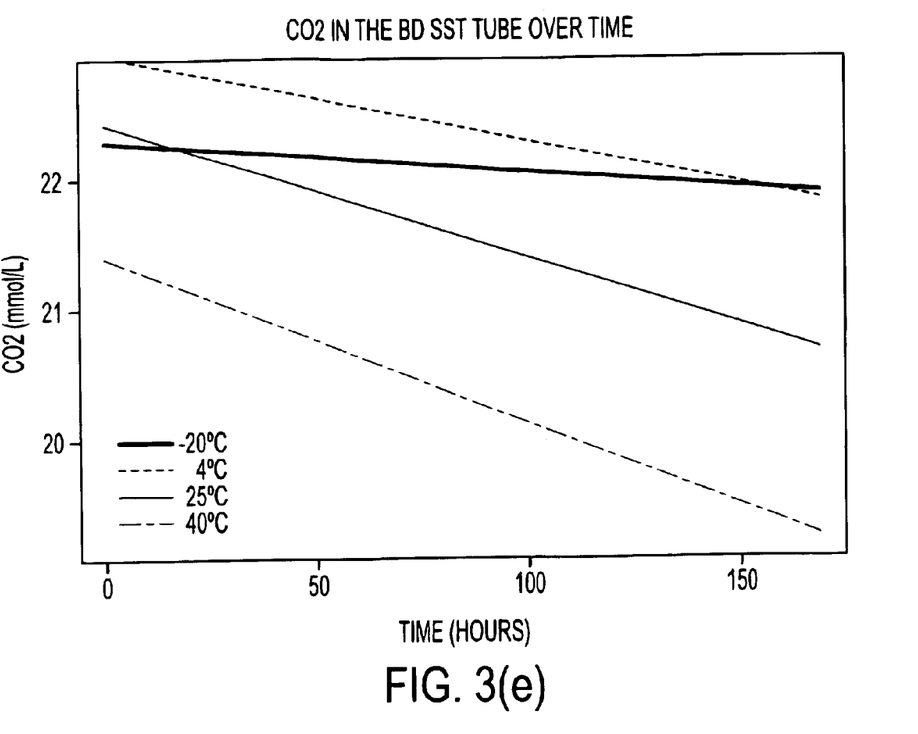
FIG. 3(e) is a graph illustrating analyte value verses time for four separate temperature values.
Figure 4A:
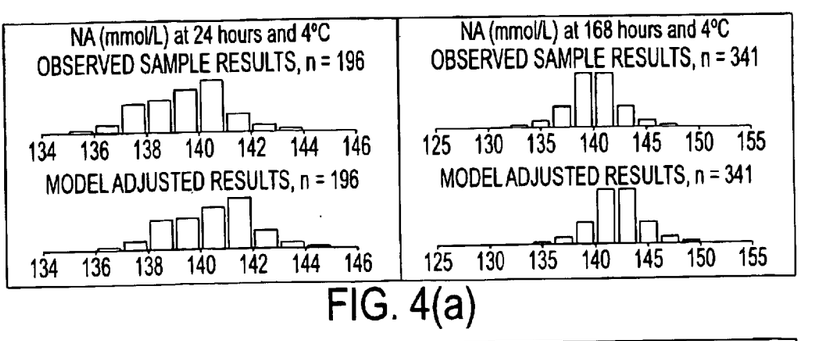
FIGS. 4(a)–(g) are histograms comparing the differences between predicted initial results and actual initial results to the differences between aged actual results and actual initial results.
Figure 4B:
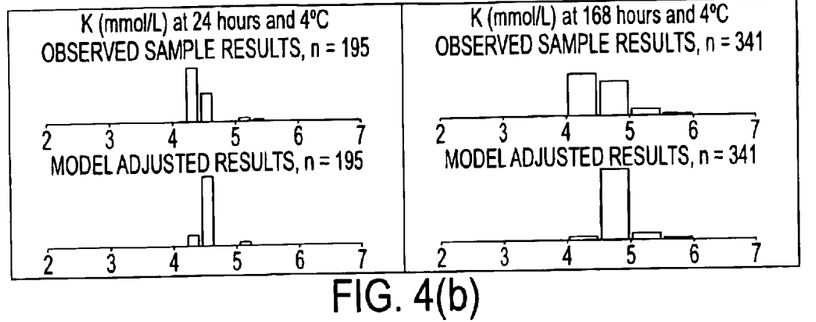
Figure 4C:
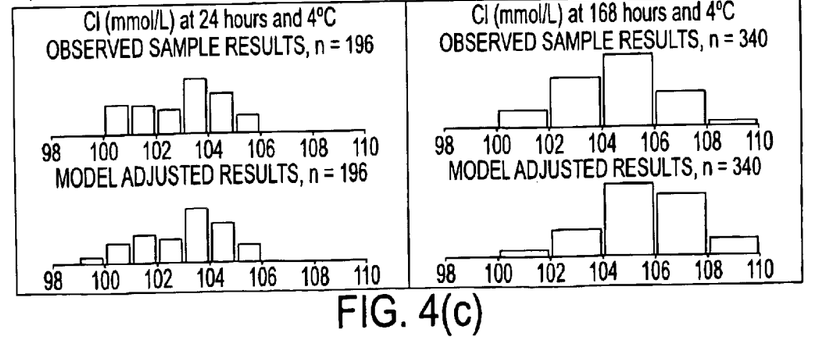
Figure 4D:
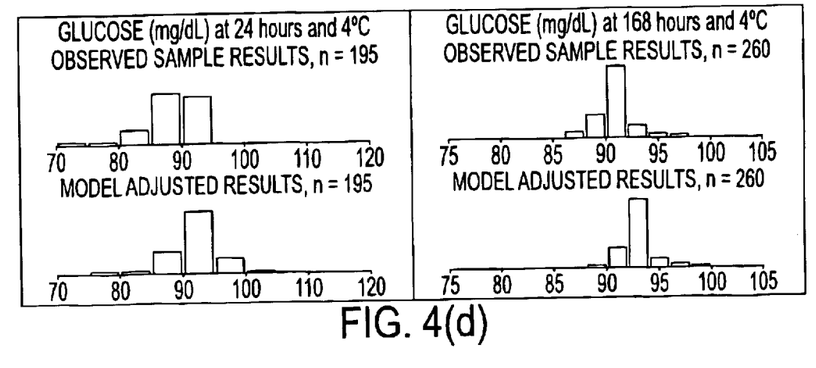
Figure 4E:
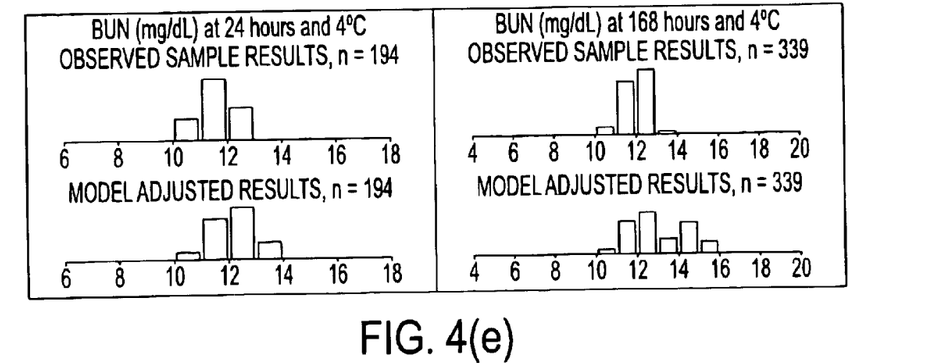
Figure 4F:
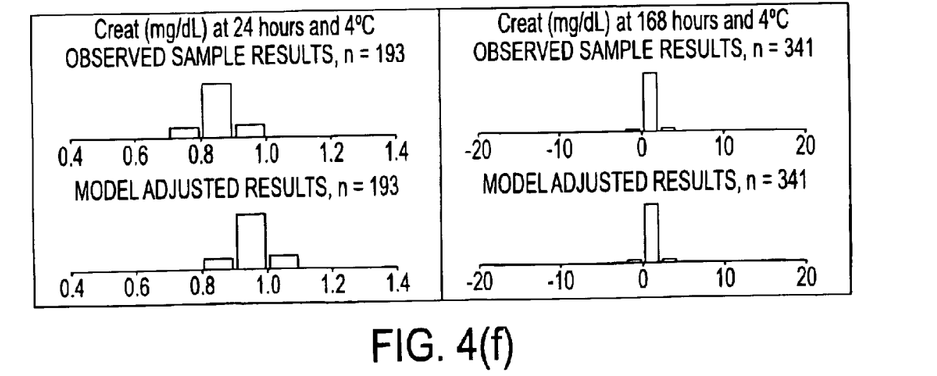
Figure 4G:
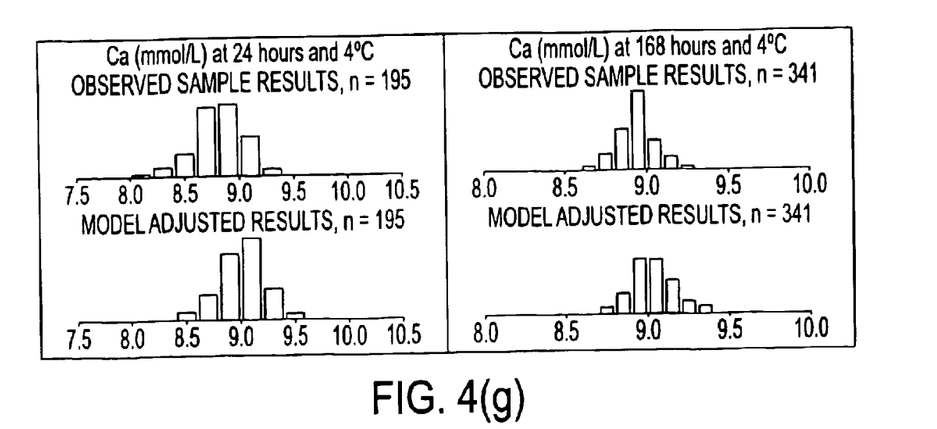

FIG. 3(e) shows an accumulation of data for various temperatures. Each line illustrated in FIG. 3(e) represents the analyte value over time at a different temperature.

The following set of exemplary equations were generated for a particular analyte, Calcium. One equation is presented for each tube type:

| Calcium | Plain Tube | $Ca = 9.47855 − 0.00698 (Time) + 0.00024 (Temp) + 0.00004 (Temp)^2$ |
|---|---|---|
| | SST Tube | $Ca = 9.39084 − 0.00698 (Time) + 0.00482 (Temp) + 0.00004 (Temp)^2$ |
| | Eval Tube | $Ca = 9.27934 − 0.00698 (Time) + 0.00914 (Temp) + 0.00004 (Temp)^2$ |

Of course it will be understood that the above equations could be presented in other formats. For instance, a single equation could be presented which takes tube type into account as a variable. Furthermore, an equation or set of equations could be presented which do not include temperature as a variable, but rather assume a certain temperature. In other words, a set of equations could be presented, one equation per temperature. Of course any variety of equations could be presented, depending on the needs of a particular situation. The above representative equation is not meant to be limiting, but rather is presented merely as illustrative of the invention. A wide variety of equations are contemplated to be within the scope of the invention.

Certain variables, such as container type, do not lend themselves to standard incorporation into an equation as do continuous variables such as time and temperature. For a variable such as container type, a "dummy" variable can be used. As an example, a particular study may include three types of sample containers. The equation generated can have three variables, one for each type of container, which will have a value of zero or one, depending on which particular container was used. In this manner, the data collected may be aggregated according to container type. Thus, one equation or model can be generated for each container type, or alternatively, a single equation can be generated having a variable for each container type. In this manner, the model generated would be valid for the container types included in the study, but more data may need to be acquired in order to generate a valid model for a new container type.

Validation of Predictive Model

The models were validated with independent patient data sets. Initial results for each patient were predicted based on the patient result observed at a latter time, the storage time, the storage temperature, and the type of tube used for sample collection. The true initial results were known for the validation data, and the differences between the model-based predictions and the true initial results were calculated. The percent values occurring within clinical acceptance limits of the initial value (time=0) were calculated for repeat observed values and the predicted values.

To evaluate the models, the differences between the model predictions and the true initial results were compared to the differences between the aged sample results and the true initial results. This mimics the real situation where the ages sample result substitutes for the initial result. Vertically stacked histograms, shown in FIGS. 4(a)–(g), are used to compare the two sets of differences. The histograms shown in FIGS. 4(a)–(g) represent both precision and accuracy of the estimate for a typical patient. The donor's "true" value is the midpoint of the interval shown on the horizontal axis. The histograms in the top row of each of FIGS. 4(a)–(g) represent the differences between the aged observed sample results and the true observed initial results. The histograms in the bottom rows represent the differences between the model-adjusted predictions of initial value and the true observed initial results.

Figure 5:
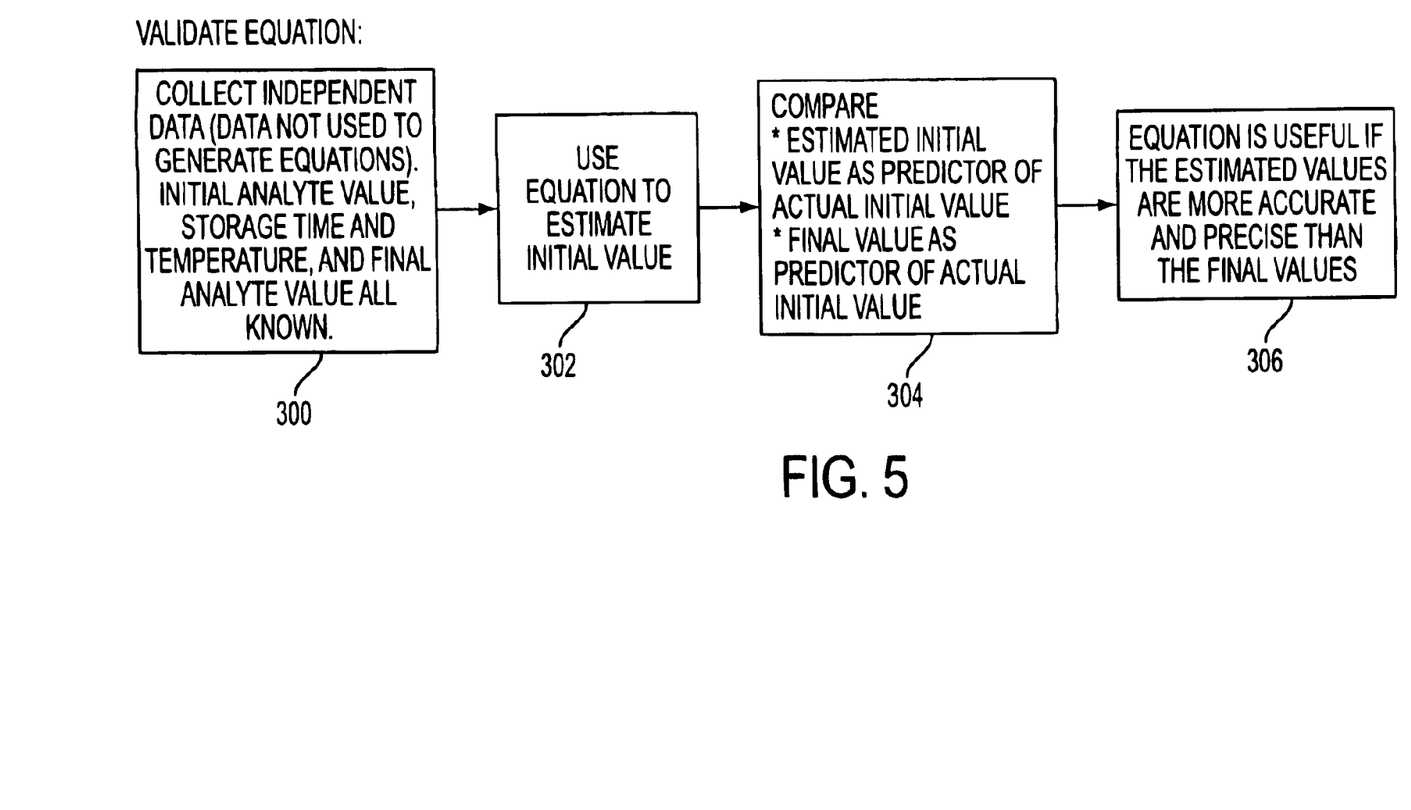
FIG. 5 is a flowchart depicting a method of predicting initial analyte values using a predictive model in accordance with an embodiment of the present invention.

The process of validating predictive models is illustrated in FIG. 5. First, at step 300, a set of samples are taken, and data are collected. The set of samples taken for validation is preferably different from the set used to generate the predictive models. In the validation set of data, the initial analyte value, the storage time, temperature, and storage tube type, as well as the final analyte value are all known. At step 302, the predictive model is used to estimate the initial values of analytes in the validation set. At step 304, the estimated initial value is compared to the actual observed final value. Finally, at step 306, the equation is determined to be useful if the estimated (predicted) initial values are more accurate and more precise than the actual observed final values.

Using the Predictive Model

Figure 6:
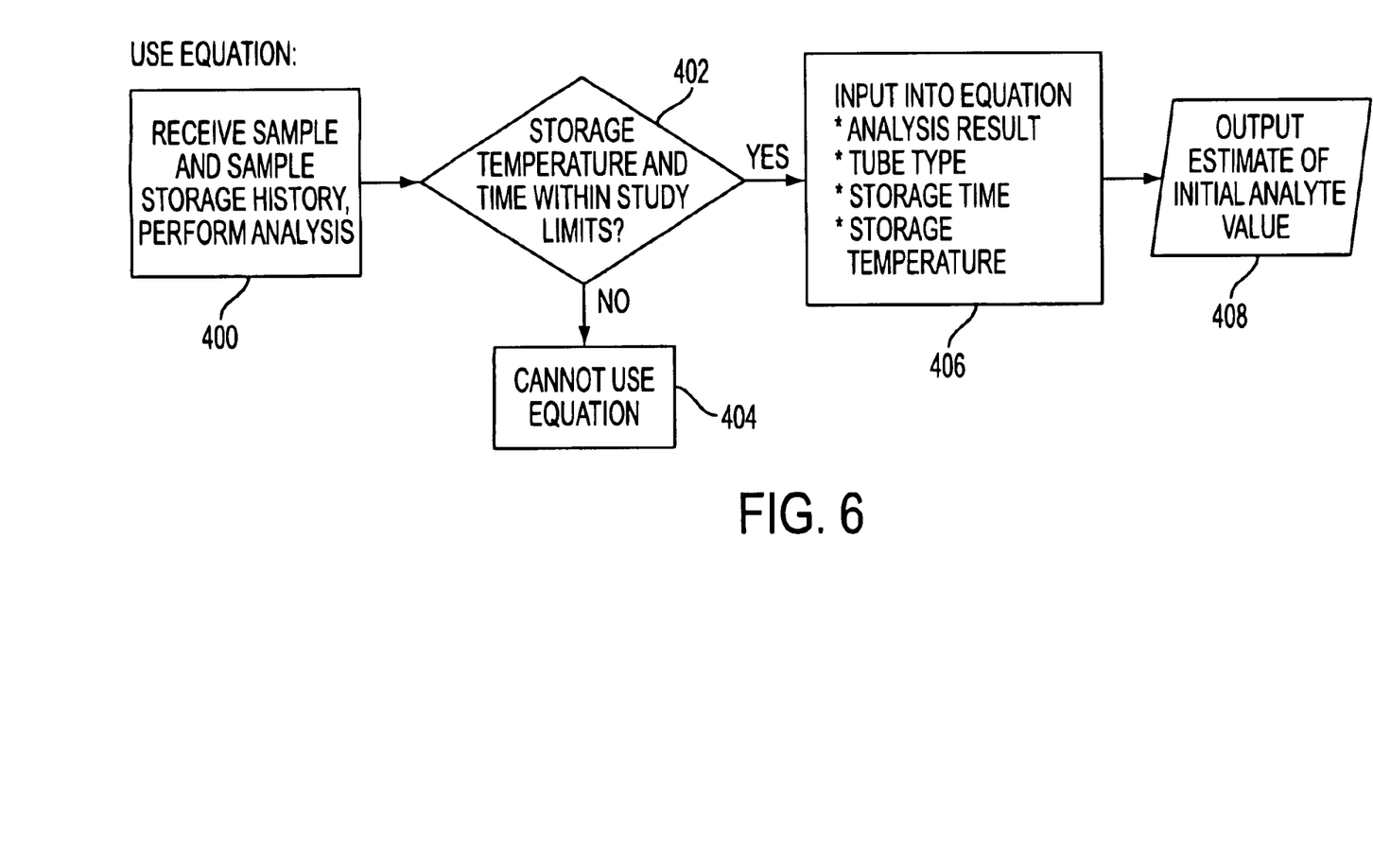
FIG. 6 is a flowchart depicting a method of validating a predictive model as used in an embodiment of the present invention.

The flowchart of FIG. 6 illustrates the process of using the predictive model to determine an unknown initial analyte value from a sample which has been stored under known conditions, including known time, temperature, and tube type. At step 400, the sample is received, including data related to the storage history of the sample. Analysis is performed on the sample to determine actual present analyte values. The temperature and time of storage, and the tube type are checked at step 402 to determine if they are within study limits. If they are not, the predictive model cannot reliably be used (step 404). If the values are within study limits, then at step 406, the actual analysis result, along with data pertaining to the tube type, storage time, and storage temperature are input to the predictive model. The equation is calculated, and at step 408, the estimated initial analyte value is output.

The present invention may be used in a variety of manners, and it should be understood that it is anticipated that the invention could be practiced in ways other than those specifically described herein. As an example, in addition to clinicians and labs using the present invention to determine estimated initial analyte values, the present invention could be used as a quality assurance tool. Depending on the type of information available, the predicted initial analyte value could be used in a quality assurance setting to trigger further investigation into methods and procedures to remove sources of error. In a first type of scenario, predicted initial analyte values could be compared to prior history for a particular patient. In this setting, if the difference between the predicted initial value and expected value based on the patient's history exceeds some threshold, further investigation could be triggered. In a second type of situation, if actual initial analyte values are known, then the actual initial analyte value could be compared to the predicted initial value. In a third scenario, in which a batch of samples from a group of patients is available, the differences between measured value and estimated initial value could be compared across the samples for statistical consistency. Also, where a group of patient histories are available, the set of predicted initial values could be compared to the set of patient histories to determine if the deviations are consistent. Any statistical anomalies in the estimated change in analyte value among the batch of samples could trigger further investigation.

While the invention herein disclosed has been described by means of specific embodiments and applications thereof, numerous modifications and variations could be made thereto by those skilled in the art without departing from the scope of the invention as set forth in the claims.

What is claimed is:

1. A method of predicting an initial value of an analyte in a sample, said method comprising the steps of:
    making a plurality of observations on a plurality of samples, wherein each observation includes a plurality of variables associated with said samples,
    generating an equation which approximates said plurality of observations, said equation containing a quadratic term for storage time, a quadratic term for storage temperature, and a mixed term for storage time and storage temperature,
    measuring a sample analyte value after storing said sample for a known non-zero time, said sample having associated therewith a container type, a storage time, and a storage temperature,
    inputting said container type, said storage time, said storage temperature, and said analyte value into said equation, and
    solving said equation to obtain an estimated initial analyte value.

2. The method of claim 1, further comprising the step of solving said equation for initial analyte value as a function of container type, storage time, and storage temperature.

3. The method of claim 1, wherein said sample is a blood sample.

4. The method of claim 1, wherein the plurality of variables associated with said sample comprises an actual initial analyte level, an actual subsequent analyte level, a time since the sample was taken, and a temperature at which said sample was stored.

5. The method of claim 1, wherein the plurality of variables associated with said sample comprises an actual initial analyte level, an actual subsequent analyte level, a time since the sample was taken, and a type of container in which said sample was stored.

6. The method of claim 1, wherein the plurality of variables associated with said sample comprises an actual initial analyte level, an actual subsequent analyte level, a temperature at which the sample was stored, and a type of container in which said sample was stored.

7. The method of claim 1, wherein the plurality of variables associated with said sample comprises an actual initial analyte level, an actual subsequent analyte level, a time since the sample was taken, a temperature at which said sample was stored, and a type of container in which said sample was stored.

8. A method of predicting an initial value of an analyte in a sample, said method comprising the steps of:
    determining a level of an analyte in a sample after storing said sample for a known non-zero time, said sample having associated therewith at least one factor selected from the group consisting of a container type, a storage time, and a storage temperature,
    inputting said at least one factor and said analyte level into an equation, said equation containing a quadratic term for storage time, a quadratic term for storage temperature, and a mixed term for storage time and storage temperature, and
    solving said equation to obtain an estimated initial analyte value.

9. The method of claim 8, wherein said equation represents analyte level as a function of storage time.

10. The method of claim 8, wherein said equation represents analyte level as a function of storage temperature.

11. The method of claim 8, wherein said equation represents analyte level as a function of container type.

12. The method of claim 8, wherein said equation represents analyte level as a function of storage temperature and storage time.

13. The method of claim 8, wherein said equation represents analyte level as a function of storage temperature and container type.

14. The method of claim 8, wherein said equation represents analyte level as a function of storage time and container type.

15. The method of claim 8, wherein said equation represents analyte level as a function of storage temperature, storage time, and container type.

16. The method of claim 8, wherein said sample is a blood sample.

17. A system for estimating an initial value of an analyte in a sample, said system comprising:
    an analyzer adapted to analyze the actual level of an analyte in a sample,
    an estimator adapted to estimate said initial value of said analyte based on a plurality of variables, said variables including said actual level of said analyte, a storage time, a storage temperature, and a container type, and
    an output adapted to present said estimated initial value;
    wherein said estimator estimates said initial level using an equation associated with said analyte, said equation adapted to solve for initial analyte level as a function of actual analyte level, storage time, storage temperature, and container type; and
    wherein said equation contains a quadratic term for time, a quadratic term for temperature, and a mixed term for time and temperature.

18. The system of claim 17, wherein said sample is a blood sample.

* * * * *